United States Patent [19]

Sterling et al.

[11] Patent Number: 5,466,683
[45] Date of Patent: Nov. 14, 1995

[54] WATER-SOLUBLE ANALOGS OF CARBAMAZEPINE

[75] Inventors: Jeff Sterling, Jerusalem; Yaacov Herzig, Raanana, both of Israel

[73] Assignee: Teva Pharmaceutical Industries Ltd., Netanya, Israel

[21] Appl. No.: 296,363

[22] Filed: Aug. 25, 1994

[51] Int. Cl.$^6$ .......................... A61K 31/55; A61K 31/675; C07D 223/28; C07F 9/553
[52] U.S. Cl. ............................ 514/80; 514/217; 540/542; 540/589
[58] Field of Search ...................................... 540/542, 589; 514/80, 217

[56] References Cited

U.S. PATENT DOCUMENTS

| | | | |
|---|---|---|---|
| 3,185,679 | 5/1965 | Schindler et al. | 260/239 |
| 3,637,661 | 1/1972 | Schindler | 260/239 D |

FOREIGN PATENT DOCUMENTS

| | | | |
|---|---|---|---|
| 2017959 | 12/1990 | Canada | A61K 47/40 |
| 2033118 | 6/1991 | Canada | A61K 47/40 |
| 400609 | 12/1990 | European Pat. Off. | A61K 31/55 |
| 435826 | 7/1991 | European Pat. Off. | A61K 31/55 |

OTHER PUBLICATIONS

L. Gram et al., "Carbamazepine Toxicity," *Antiepileptic Drugs*, Third Edition, Ed. R. Levy et al., New York: Raven Press, Ltd. (1989), pp. 555–565.

M. Dam et al., "Potential Antiepileptic Drugs: Oxcarbazepine," *Antiepileptic Drugs*, Third Edition, Ed. R. Levy et al., New York: Raven Press, Ltd. (1989), pp. 913–924.

R. Heckendorn, "Synthesis of trans–10,11–Dihydro–10, 11–dihydroxy–5H–dibenz[b,f]azepine–5–carboxamide, a Major Metabolite of Carbamazepine," *Helvetica Chimica Acta*, vol. 70 (1987), pp. 1955–1962.

E. A. Swinyard et al., "General Principles: Experimental Selection, Quantification, and Evaluation of Anticonvulsants," *Antiepileptic Drugs*, Third Edition, Ed. R. Levy et al., New York: Raven Press, Ltd. (1989), pp. 85–102.

S. A. Varia et al., "Phenytoin Prodrugs III: Water–Soluble Prodrugs for Oral and/or Parenteral Use," *Journal of Pharmaceutical Sciences*, vol. 73, No. 8, Aug. 1984, pp. 1058–1059; 1070–1073.

R. D. Smith et al., "Pharmacology of ACC–9653 (Phenytoin Prodrug)," *Epilepsia*, vol. 30, Suppl. 2, (1989), pp. S15–S21.

*Primary Examiner*—Philip I. Datlow
*Attorney, Agent, or Firm*—Darby & Darby

[57] ABSTRACT

The present invention relates to novel water-soluble analogs of carbamazepine and compositions containing them. The novel compositions are particularly suited for intravenous administration. The analogs of carbamazepine are useful in the treatment of epilepsy and related disorders.

17 Claims, No Drawings

WATER-SOLUBLE ANALOGS OF CARBAMAZEPINE

FIELD OF THE INVENTION

The present invention relates to novel water-soluble analogs of carbamazepine and their use in the treatment of epilepsy.

BACKGROUND OF THE INVENTION

Carbamazepine (5H-dibenz[b,f]azepine-5-carboxamide, CBZ), is a major drug used in the treatment of epileptic seizures and convulsions as well as in trigeminal neuralgia. However, in the treatment of epilepsy, approximately 25% of patients fail to respond to treatment. Furthermore, CBZ itself is associated with considerable adverse side effects, as described by L. Gram and P. K. Jensen in *Antiepileptic Drugs*, ed. R. H. Levy et al., Raven Press, N.Y. (1989), pages 555–565.

10-Oxo-carbamazepine (OCBZ) has been reported to be as active as CBZ, whilst exhibiting a smaller incidence of less severe side effects. It has been found to be of particular use in the treatment of patients suffering from generalized tonic-clonic convulsions and partial seizures with or without secondary generalization. The activity of OCBZ is attributed to its metabolite 10-hydroxy-10,11-dihydrocarbamazepine (DHOHCBZ); see M. Dam and P. K. Jensen in *Antiepileptic Drugs*, supra, pages 913–924.

Despite the favorable activity of these compounds, a drawback in their clinical use arises from their low solubility in aqueous media. It would be of considerable benefit if water-soluble derivatives of these compound existed and could therefore be administered intravenously. Such a route of administration would be especially beneficial in the treatment of Status Epilepticus. Water-soluble formulations of CBZ and OCBZ have been described in European Patent Applications, Publication Nos. 400609 and 435826, both of Ciba-Geigy. These formulations are obtained by formulating the drugs with cyclodextrin derivatives.

Another difficulty with the prior art is the lack of an efficient and inexpensive preparation of DHOHCBZ. Several routes have been proposed. For example, DHOHCBZ has previously been prepared by hydrogenating OCBZ under high temperature and pressure as described in U.S. Pat. No. 3,637,661 of Ciba-Geigy. Reduction by $NaBH_4$ of the keto functionality in the benzo{b,f}-azepine series has been described for the 10-oxo-11-acetate derivative of CBZ (see R. Heckendorn, *Helv. Chim. Acta* (1987) 70, 1955, 1956) and for 10-oxo-5-dialkyl-aminoalkyl derivatives in U.S. Pat. No. 3,185,679 of Geigy.

SUMMARY OF THE INVENTION

The present invention seeks to provide novel water-soluble analogs of carbamazepine suitable for use in the treatment of epilepsy and related disorders and a method for the preparation of DHOHCBZ directly from OCBZ under surprisingly mild conditions.

A first embodiment of the invention are compounds of general formula I:

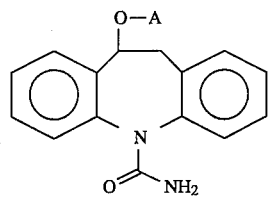

wherein A is an amino acyl moiety of formula II:

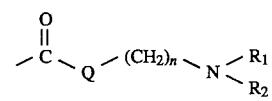

or a phosphonyl or sulphonyl group of formula III:

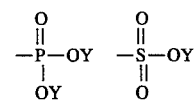

wherein Q is a phenylene group or CHR; R is hydrogen or a $C_1$–$C_4$ alkyl group; n is from 0 to 4; $R_1$ and $R_2$ are each independently hydrogen or a $C_1$–$C_4$ alkyl group; and Y is hydrogen or an alkali metal.

These compounds are water-soluble and are believed to be as active as both CBZ and OCBZ.

In another embodiment of the invention, DHOHCBZ is prepared directly from OCBZ by reduction with $NaBH_4$ in methanol under mild conditions of temperature and pressure.

One of the unique aspects of the present invention is that the hydroxyl derivative of OCBZ, rather than the drug itself, is used as the starting material to obtain water-solubility. This will be noted from the prior art, particularly EP 400,609 and EP 435,826. With respect to carbamazepine, conventionally it has been formulated with cyclodextrin in an effort to obtain a water-soluble formulation. Since the hydroxyl derivative is not bioreversible to the CBZ itself, it is quite surprising that a highly effective water-soluble drug can be obtained by following the process of the invention. This advantage arises out of the choice of the appendant groups A as defined above. In certain embodiments of the present invention, a further advantage is the release of the CNS active amino acids glycine and gamma-aminobutyric acid (GABA) upon hydrolysis.

DETAILED DESCRIPTION OF THE INVENTION

It is preferred that A is formula II, Q is CHR, R, $R_1$ and $R_2$ are hydrogen, and n=0 or 2. In an alternative embodiment, it is preferred that A is sulphonyl or phosphonyl group, preferably phosphonyl, and Y is sodium.

Examples of the preferred compounds are: 10-O-(2-aminoacetyl)-10,11-dihydrocarbamazepine hydrochloride, 10-O-(4-aminobutyroyl)-10,11-dihydrocarbamazepine hydrochloride, 10-O-phosphonyl-10,11-dihydrocarbamazepine disodium salt, and 10-O-sulphonyl-10,11-dihydrocarbamazepine disodium salt.

The compounds of the present invention possess chiral centers. A further embodiment of the invention relates to the substantially pure enantiomers of these compounds. The enantiomers may be isolated by methods known to those skilled in the art.

Without wishing to be limited by any suggested mechanism of action, the compounds of the present invention are believed to act as water-soluble prodrugs of 10-hydroxy-10, 11-dihydrocarbamazepine, the active metabolite of OCBZ.

By administering to a patient an effective amount of the compounds of the invention, the following illnesses and disorders may be effectively treated:

epilepsy;

affective illness;

cognitive disorders;

neurodegenerative disease;

dyskinesiae;

convulsions.

The compounds of the invention are administered in pharmaceutical compositions which comprise the compound and a pharmaceutically acceptable carrier. As used herein, the term "pharmaceutically acceptable carrier" encompasses any of the standard pharmaceutically accepted carriers, such as a phosphate-buffered saline solution, water, an oil/water or a triglyceride emulsion, wetting agents, tablets, coated tablets, and capsules. An example of an acceptable triglyceride emulsion useful in the intravenous and intraperitoneal administration of the compounds is the triglyceride emulsion commercially known as Intralipid® (a trademark of KabiVitrum (UK).

Generally, the amount of the carrier is from 5 to 95 wt. % of the total formulation.

Typically, such carriers contain excipients such as starch, milk, sugar, certain types of clay, gelatin, stearic acid, talc, vegetable fats or oils, gums, and glycols. Such carriers may also include flavor and color additives or other ingredients. The optimum amounts of such materials may be readily determined by those skilled in the art.

In the practice of the invention, the pharmaceutical composition may be administered by any of the well-known methods, including, but not limited to, oral, intravenous, intraperitoneal, intramuscular or subcutaneous or topical administration. Topical administration can be effected by any method commonly known to those skilled in the art and include, but are not limited to, incorporation of the pharmaceutical composition into creams, ointments, or transdermal patches.

The amount of the compound incorporated in the pharmaceutical composition may vary widely. Factors considered when determining the precise amount are well known to those skilled in the art. These include the characteristics of the subject being treated, the specific pharmaceutical carrier, the route of administration, and the frequency with which the composition is to be administered. A pharmaceutical composition in unit dose form for treatment of the disorders listed hereinabove contains from 10 to 500 mg of the active ingredient.

Preferably the pharmaceutically acceptable carrier is an aqueous liquid and the composition is a solution. Such compositions are suitable for administration via intravenous and oral liquid routes, these being of particular benefit in the treatment of children.

Turning to the processes of the invention, the compounds of formula I wherein A is of formula II are amino acid esters of DHOHCBZ and may be prepared by esterification, for example, by reacting an activated form of the amino acids with DHOHCBZ in the presence or absence of acylation catalysts such as 4-N,N-dimethylaminopyridine (DMAP), pyridine, cobalt (II) chloride, and acids and bases, particularly Lewis acids and bases. Examples of activated or functionalized forms of the amino acids are:

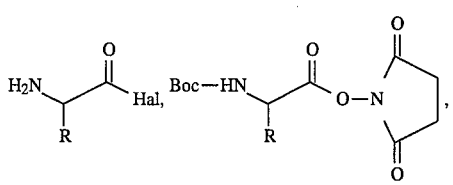

(Boc-glycine-N-hydroxysuccinimide ester)

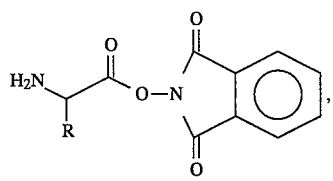

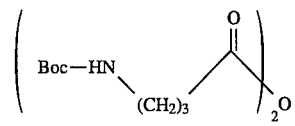

(Boc-GABA anhydride)

Thus, for example, DHOHCBZ is reacted with an amino acid anhydride having a protected amino terminus, e.g., with a t-butoxycarbonyl (Boc) radical, in the presence of, for example DMAP, in an aprotic organic solvent, e.g., tetrahydrofuran (THF), 1,2-dimethoxyethane (DME), dichloromethane and dioxane, at a temperature of from 0° to 50° C., preferably from 25° to 40° C., for a period of from 1 to 24 hours, preferably 5 hours. In this reaction, each mole of DHOHCBZ is preferably reacted with 1 to 1.5 moles of the activated amino acid. From 20 to 100 ml of solvent are used for each gram of the DHOHCBZ.

Alternatively, DHOHCBZ may be reacted with a N-succinimide ester of an amino acid having the amino terminus protected, e.g., by a Boc radical, in an aprotic organic solvent at a temperature of from 0° to 70° C., preferably from 25° to 50° C., for a period of from 12 to 48 hours, preferably from 24 to 36 hours. The ratio of the DHOHCBZ to amino acid and the amount of solvent used are as described above.

The esterified product may be purified by column chromatography, by which excess Boc-glycine-succinimide may be removed after having been converted to the corresponding methyl ester by treating the crude product with methanol.

Removal of the protecting group may be accomplished by any means known to those skilled in the art, as for example by subjecting the protected acyl DHOHCBZ to acidic conditions, e.g., trifluoroacetic acid or solutions of hydrochloric acid in an organic solvent, e.g., dioxane. The DHOHCBZ derivatives are then obtained as the acid salts and are readily soluble in water.

The compounds of formula I, wherein A is a phosphonyl group of formula III, are phosphate esters of DHOHCBZ and may be prepared by subjecting the latter to one of the following procedures: reacting DHOHCBZ with (a) phosphorus oxychloride in a polar aprotic solvent in the presence of an acid acceptor, followed by sodium hydrogen carbonate; or (b) 2-cyanoethyl-N,N-diisopropyl-chlorophosphoramidite, followed by tetrazole and 2-cyanoethanol, by t-butylhydroperoxide and finally by ammonia. Suitable polar aprotic solvents include acetonitrile and acid acceptors, e.g., N,N-diisopropylethylamine. The reaction temperature may be from ambient to 80° C. for a period of from 5 to 100 hours. The DHOHCBZ derivative is then obtained as the corresponding metal salt and is readily soluble in water.

The compounds of formula I, wherein A is a sulphonyl group of formula III, are sulfate esters of DHOHCBZ and may be prepared by reacting DHOHCBZ with sulphotrioxide-triethylamine or sulphotrioxide-trimethylamine in a polar protic or aprotic solvent, e.g., water, dimethylformamide and pyridine at temperature of from ambient to 100° C., preferably to 80° C., and purification by column chromatography. The sulphonic acid may be converted to an alkali salt by treatment with an ion exchange resin such as Dowex 50.

The following experimental details are set forth to aid in an understanding of the invention, and are not intended, and should not be construed, to limit in any way the invention set forth in the claims which follow thereafter.

EXAMPLES

EXAMPLE 1

10-O-(2-N-Boc-aminobutyroyl)-10,11-dihydrocarbamazepine

A solution of GABA anhydride (1.84 g, 4.7 mmol, prepared from Boc GABA and dicyclohexylcarbodiimide in $CH_2Cl_2$) in THF (27 ml) was added to a solution of DHOHCBZ (1.0 g, 3.94 mmol) in THF (50 ml), followed by the addition of 4-N,N-dimethyl-aminopyridine (480 mg, 3.93 mmol). The clear solution was stirred at ambient temperature for 6 hours and evaporated to dryness. The residue was dissolved in EtOAc (40 ml), washed with saturated $NaHCO_3$ (3×15 ml) and water (3×15 ml), dried ($MgSO_4$) and evaporated to dryness under reduced pressure to give 1.7 g (3.87 mmol, 82%) of the title compound, m.p. 148–150° C.

$^1$H-NMR ($CDCl_3$): 7.50–7.20 (m, 8H, Ph), 6.42 (br s, $1H,C_{10}$—H), 5.20, 4.62 (br s,1H,NH), 4.82 (br d,2H, $CONH_2$), 3.60 (m,$1H,C_{11}$—H), 3.22 (m,$1H,C_{11}$—H), 3.16 (m,2H,GABA-CγH), 2.38 (t,2H,GABA-CαH), 1.80 (m,2H, GABA-CαH), 1.44 (s,9H,Boc) ppm.

MS: 440($MH^+$, 42), 340 ($MH^+$-BocNH, 59), 237 ($MH^+$-BocGABA, 100).

EXAMPLE 2

10-O-(2-aminobutyroyl)-10,11-dihydrocarbamazepine.HCl

10-O-(2-N-Boc aminobutyroyl)-10,11-dihydrocarbamazepine (1.25 g, 2.84 mmol) was dissolved in dry $CH_2Cl_2$ (80 ml), and 1.7N HCl in dioxane (9.2 ml) was added. The solution was stirred at ambient temperature for 3 hours, evaporated to dryness and the residue was treated with a mixture of $CH_2Cl_2$ (60 ml) and water (80 ml). The aqueous phase was separated, filtered through millipore and lyophilized, to give 900 mg (2.4 mmol, 84%) title compound.

$^1$H-NMR ($D_2O$): 7.60–7.20 (m,8H,Ph), 6.36, 5.70 (br s,$1H,C_{10}$—H), 3.53 (m,$1H,C_{11}$—H), 3.15 (m,$1H,C_{11}$—H'), 2.98 (m,2H,GABA-CγH), 2.50 (m,2H,GABA-CαH), 1.93 (m,2H,GABA-CβH) ppm.

MS: 340($MH^+$, 12), 237 ($MH^+$-GABA,100), 194 (58).

EXAMPLE 3

10-O-(2-N-BOC aminoacetyl)-10,11-dihydrocarbamazepine

A solution of DHOHCBZ (940 mg, 3.7 mmol) and Boc-glycine-N-hydroxysuccinimide ester (1.0 g, 3.7 mmol) in anhydrous 1,2-dimethoxyethane (40 ml) was stirred for 36 hours at ambient temperature. The residue obtained after the removal of solvent was treated with methanol (20 ml, RT, 10 min). The solution was evaporated to dryness and the residue was dissolved in EtOAc (10 ml) and washed with $NaHCO_3$ (10 ml) and water. The organic phase was dried over $MgSO_4$ and evaporated to dryness. The crude product was purified by column chromatography ($SiO_2$, toluene:acetone 70/30) to afford 890 mg (2.17 mmol, 59%) of title compound, m.p. 79–80° C.

$^1$H-NMR ($CDCl_3$): 7.5–7.20 (m,8H,Ph), 4.85 (br d,2H, $CONH_2$), 1.45 (s,9H,Boc).

major conformer: 6.05 (br s,$1H,C_{10}$—H), 5.04 (br s,1H, $C_{11}$—H), 3.60 (m,$1H,C_{11}$—H), 3.23 (m,$1H,C_{11}$—H').

minor conformer: 6.47 (br s,$1H,C_{10}$—H), 5.22 (br s,1H, NH), 3.67 (m,$1H,C_{11}$—H), 3.10 (m,$1H,C_{11}$—H') ppm.

MS: 412($MH^+$, 82), 356 ($MH^+$-$C_4H_8$, 88 ), 237 ($MH^+$-Boc gly, 100).

EXAMPLE 4

10-O-(2-aminoacetyl)-10,11-dihydrocarbamazepine.HCl

10-O-(2-N-Boc-aminoacetyl)-10,11-dihydrocarbamazepine (830 mg, 2.67 mmol) was dissolved in dry $CH_2Cl_2$ (60 ml), and 1.7N HCl in dioxan (7 ml) was added. The clear solution was stirred at ambient temperature for 3 hours, evaporated to dryness under reduced pressure. The residue was dissolved in water (50 ml), extracted with $CH_2Cl_2$ (30 ml), filtered through millipore and evaporated to dryness under reduced pressure, to give 600 mg (1.73 mmol, 65%) of the title compound.

$^1$H-NMR ($D_2O$): 7.50–7.20 (m,8H,Ph) , 3.88 (m,$2H,CH_2$) .

major conformer: 6.12 (m,$1H,C_{10}$—H), 3.56 (m,1H, $C_{11}$—H), 3.24 (m,$1H,C_{11}$—H').

minor conformer: 6.51 (br s,$1H,C_{10}$—H), 3.62 (m,1H, $C_{11}$—H); 3.16 (m,$1H,C_{11}$—H') ppm.

MS: 312 ($MH^+$, 53), 237 ($MH^+$-gly, 89) 194 (237-NHCO, 100).

EXAMPLE 5

Sodium-10-O-sulphate-10,11-dihydrocarbameazepine

A solution of DHOHCBZ (254 mg, 1 mmole) and $SO_3Me_3N$ (417 mg, 3 mmole) in dry THF (4 ml) was heated to 50° C. and stirred at this temperature for 3 hours. It was then evaporated to dryness under reduced pressure and the oily residue was purified by column chromatography (silica, $CH_2Cl_2$:MeOH 85:15). Treatment of the crude product with EtOAc (3 ml, 15 min, RT) gave 270 mg (81%) of a yellowish crystalline solid. The latter was converted to the corresponding sodium salt by passing through a Dowex 50 (sodium form) column. The following data relate to the free acid.

$^1$H NMR (DMSO): 7.75–7.20 (m,8H,Ph), 5.93,5.61 (m,$1H,C_{10}$—H), 3.70 (m,$1H,C_{11}$—H), 3.25 (m,$1H,C_{11}$—H) ppm

EXAMPLE 6

Biological Activity of Compounds of Formula I

All compounds provided herein were screened for their ability to protect against chemically and electrically induced convulsions, in at least two different models of epilepsy. The first model, the subcutaneous pentylenetetrazol (scMet) seizure threshold test, is a standard screening procedure to show efficacy for agents against absence seizures. The second model, the maximal electroshock (MES) test, is used to show efficacy for antiepileptic agents against generalized seizures. In these studies, convulsions were inhibited or prevented in mice after intraperitoneal (i.p.) administration and/or in rats after oral (p.o.) administration of the compounds. For detailed procedures of the above test models, see E. A. Swinyard et al., in *Antiepileptic Drugs*, supra, at pp. 85–102 (1989).

The results of these experiments are shown in Table 1 below. In Table 1, Compound No. refers to the relevant Example number. Results given for the MES and scMet tests are given as the number of animals protected/total number in test group. Toxicity data are given as the number dead/total number. The figure given under each result is the dosage in mg/kg.

TABLE 1

| COMPOUND | MICE (ip) | | | RATS (po) | |
|---|---|---|---|---|---|
| | MES | scMet | Toxicity | MES | Toxicity |
| OHCBZ (mg/kg) | 3/3 (100) | 0/1 (100) | 3/8 (100) | — | — |
| Ex. 4 (mg/kg) | 3/3 (100) | 0/1 (100) | 0/8 (100) | 4/4 (50) | 0/4 (50) |
| Ex. 2 (mg/kg) | 0/3 (100) | 0/1 (100) | 7/8 (100) | 1/4 (50) | 0/4 (50) |

What is claimed is:

1. A compound of formula I;

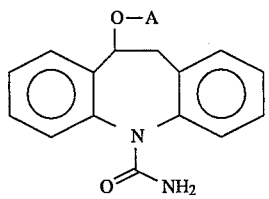

I wherein A is an amino acyl moiety of formula II:

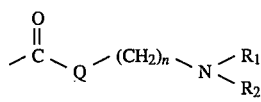

II or a phosphonyl or sulphonyl group of formula III:

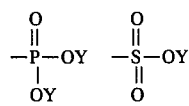

III wherein Q is a phenylene group or CHR; R is hydrogen or a $C_1$–$C_4$ alkyl group; n is from 0 to 4; $R_1$ and $R_2$ are each independently hydrogen or a $C_1$–$C_4$ alkyl group; and Y is hydrogen or an alkali metal.

2. A compound according to claim 1, wherein A is of formula II.

3. A compound according to claim 2, wherein Q is CHR.

4. A compound according to claim 3, wherein n is 0, 1 or 2.

5. A compound according to claim 4, wherein R, $R_1$ and $R_2$ are hydrogen.

6. A compound according to claim 1, wherein A is a group of formula III.

7. A compound according to claim 6, wherein A is a phosphonyl group.

8. A compound according to claim 7, wherein Y is sodium.

9. A compound according to claim 6, wherein A is sulphonyl.

10. 10-O-(2-aminoacetyl)-10,11-dihydrocarbamazepine hydrochloride.

11. 10-O-(4-aminobutyroyl)-10,11-dihydrocarbamazepine hydrochloride.

12. 10-O-phosphonyl-10,11-dihydrocarbamazepine disodium salt.

13. 10-O-sulphonyl-10,11-dihydrocarbamazepine disodium salt.

14. A method of treating a subject afflicted with epilepsy, affective illness, cognitive disorders, neuro-degenerative disease, dyskinesiae, or convulsions which comprises administering to the subject an amount of a compound according to claim 1 effective to treat said diseases in the subject.

15. A pharmaceutical composition which comprises a compound of claim 1, or a pharmaceutically acceptable salt thereof in a therapeutically effective amount and a pharmaceutically acceptable carrier.

16. A pharmaceutical composition according to claim 15 wherein the therapeutically effective amount is an amount from about 10 mg to about 500 mg.

17. A pharmaceutical composition according to claim 16, wherein the pharmaceutically acceptable carrier is a liquid and the composition is a solution.

* * * * *